(12) United States Patent
Kang et al.

(10) Patent No.: US 9,618,435 B2
(45) Date of Patent: Apr. 11, 2017

(54) UMBILICAL BEND-TESTING

(71) Applicant: DMAR ENGINEERING, INC., Houston, TX (US)

(72) Inventors: Yongtian Kang, Qingdao (CN); Dagang Zhang, Houston, TX (US); Zhiming Huang, Missouri City, TX (US); Quan Yuan, Qingdao (CN)

(73) Assignee: DMAR Engineering, Inc., Houston, TX (US)

( * ) Notice: Subject to any disclaimer, the term of this patent is extended or adjusted under 35 U.S.C. 154(b) by 273 days.

(21) Appl. No.: 14/500,928

(22) Filed: Sep. 29, 2014

(65) Prior Publication Data

US 2015/0276570 A1  Oct. 1, 2015

Related U.S. Application Data

(60) Provisional application No. 61/973,220, filed on Mar. 31, 2014.

(51) Int. Cl.
*G01N 3/08* (2006.01)
*G01N 3/20* (2006.01)
*G01M 5/00* (2006.01)

(52) U.S. Cl.
CPC ............ *G01N 3/08* (2013.01); *G01M 5/0025* (2013.01); *G01M 5/0075* (2013.01); *G01N 3/20* (2013.01); *G01N 2203/0266* (2013.01); *G01N 2203/0274* (2013.01)

(58) Field of Classification Search
CPC .. G01N 3/08; G01N 3/10; G01N 3/20; G01N 2203/0274; G01N 2203/0266; G01M 5/0075; G01M 5/0025; G01M 5/005; G01M 5/0058; G01M 5/0041
USPC .......................... 73/818, 825, 856, 857, 860
See application file for complete search history.

(56) References Cited

U.S. PATENT DOCUMENTS

| | | | | |
|---|---|---|---|---|
| 4,573,360 A * | 3/1986 | Yoneda | G01N 3/20 |
| | | | 73/850 |
| 4,625,563 A * | 12/1986 | Dawson | G01N 3/20 |
| | | | 73/850 |
| 4,677,856 A * | 7/1987 | Fischer | G01N 3/00 |
| | | | 73/850 |
| 5,231,882 A * | 8/1993 | Bertele | G01N 3/32 |
| | | | 73/852 |
| 5,606,134 A * | 2/1997 | Stieber | G01N 3/20 |
| | | | 73/849 |
| 6,619,104 B1 * | 9/2003 | Yeh | G01N 3/12 |
| | | | 73/49.1 |
| 7,277,162 B2 * | 10/2007 | Williams | E21B 47/0006 |
| | | | 356/32 |
| 7,472,604 B2 * | 1/2009 | Moore, Jr. | G01N 3/32 |
| | | | 73/841 |
| 7,980,787 B1 * | 7/2011 | Trent | E21B 19/002 |
| | | | 166/355 |
| 8,229,681 B2 * | 7/2012 | Minnaar | G01N 3/08 |
| | | | 702/187 |

(Continued)

*Primary Examiner* — Michael A Lyons
*Assistant Examiner* — Philip Cotey
(74) *Attorney, Agent, or Firm* — Liaoteng Wang

(57) ABSTRACT

Apparatus and methods related to umbilical bend-testing are described. For example, some embodiments may contain a three-level support structure, umbilical terminal locker, bending machine, compression testing device, and stress-strain collection system, and may be used for the bending fatigue endurance test for umbilical samples.

15 Claims, 10 Drawing Sheets

(56) References Cited

U.S. PATENT DOCUMENTS

| | | | | |
|---|---|---|---|---|
| 8,443,680 B2* | 5/2013 | Taylor, Jr. | G01N 3/22 | 73/849 |
| 9,372,137 B1* | 6/2016 | Patten | G01N 3/02 | |
| 2005/0087271 A1* | 4/2005 | Gejima | B21D 53/88 | 148/624 |
| 2006/0045408 A1* | 3/2006 | Jones | E21B 17/01 | 385/12 |
| 2006/0137465 A1* | 6/2006 | Lee | G01N 3/20 | 73/794 |
| 2007/0256503 A1* | 11/2007 | Wong | G01N 3/34 | 73/812 |
| 2008/0216585 A1* | 9/2008 | Cipra | G01N 3/20 | 73/851 |
| 2008/0303382 A1* | 12/2008 | Edwards, Jr. | G01L 5/102 | 310/328 |
| 2009/0208768 A1* | 8/2009 | Suzuki | G01N 3/08 | 428/544 |
| 2010/0000329 A1* | 1/2010 | Lorenz | G01N 3/04 | 73/856 |
| 2010/0005864 A1* | 1/2010 | Minnaar | G01N 3/08 | 73/49.1 |
| 2010/0089478 A1* | 4/2010 | Gudme | F16L 11/083 | 138/104 |
| 2010/0089586 A1* | 4/2010 | Stanecki | E21B 43/2401 | 166/303 |
| 2010/0212405 A1* | 8/2010 | Roberts | G01N 3/12 | 73/49.6 |
| 2010/0251838 A1* | 10/2010 | Halderman | G01N 3/04 | 73/866.5 |
| 2010/0277329 A1* | 11/2010 | Worzyk | G01M 11/086 | 340/679 |
| 2011/0000677 A1* | 1/2011 | Overfield | E21B 33/0385 | 166/336 |
| 2011/0176125 A1* | 7/2011 | Smith | G01B 11/165 | 356/32 |
| 2011/0178730 A1* | 7/2011 | Mangal | E21B 17/017 | 702/43 |
| 2011/0253377 A1* | 10/2011 | Barber | E21B 33/0355 | 166/336 |
| 2012/0279312 A1* | 11/2012 | Franklin | G01N 3/04 | 73/818 |
| 2014/0165709 A1* | 6/2014 | Clements | G01N 3/12 | 73/49.5 |

\* cited by examiner

UMBILICAL BEND-TESTING

CROSS REFERENCE TO RELATED APPLICATIONS

This application claims the benefit of U.S. Provisional App. No. 61/973,220, filed on Mar. 31, 2014, which is incorporated herein by reference.

FIELD OF PRESENT DISCLOSURE

This present disclosure relates to umbilical bend-testing. For example, the apparatus and methods disclosed herein may be used for the bending fatigue endurance test for umbilical samples.

BACKGROUND INFORMATION

Umbilicals are commonly used in oil and gas underwater field developments. Apparatus and methods can be designed to test the bending fatigue endurance properties of certain umbilical samples, and superiorities and defects of the umbilical samples can be fed back to the producer of the umbilicals so that they can optimize their products for various purposes.

DETAILED DESCRIPTION

Figure 1:
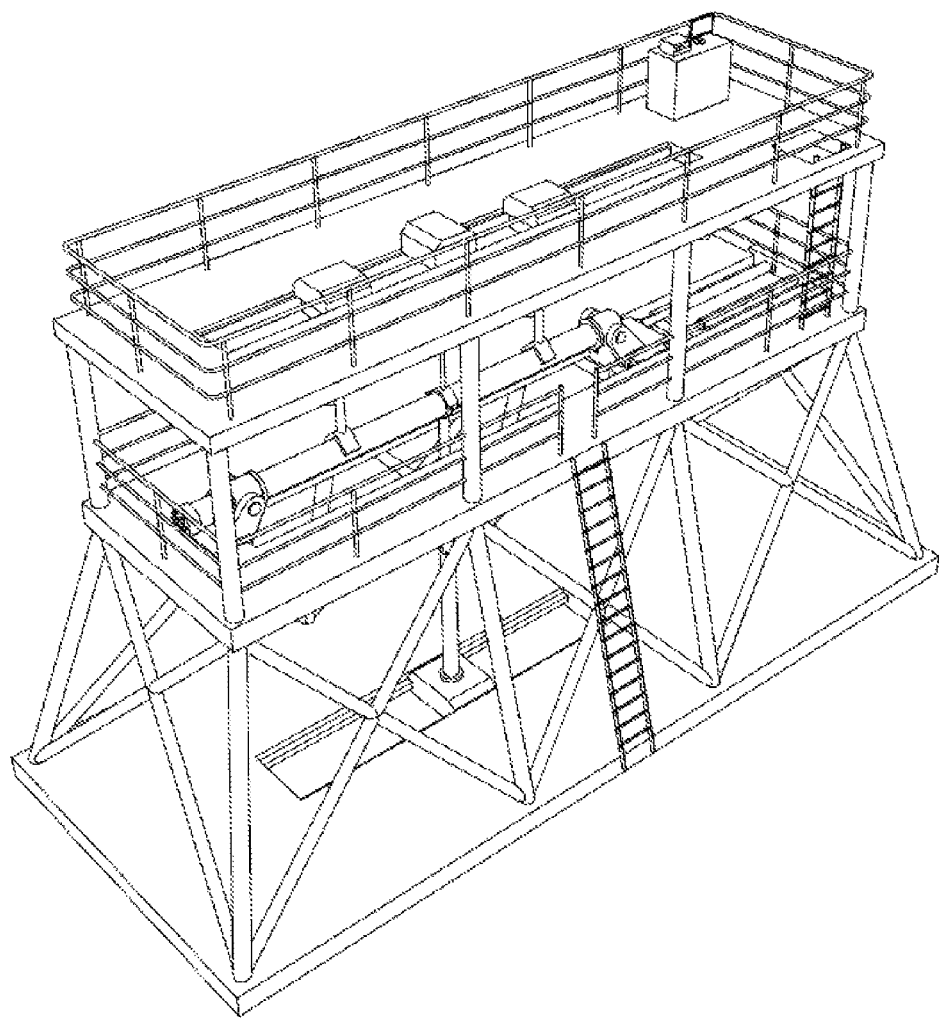
FIG. 1 is a diagram showing the perspective view of an embodiment of the apparatus and methods for umbilical bend-testing.
Figure 2:
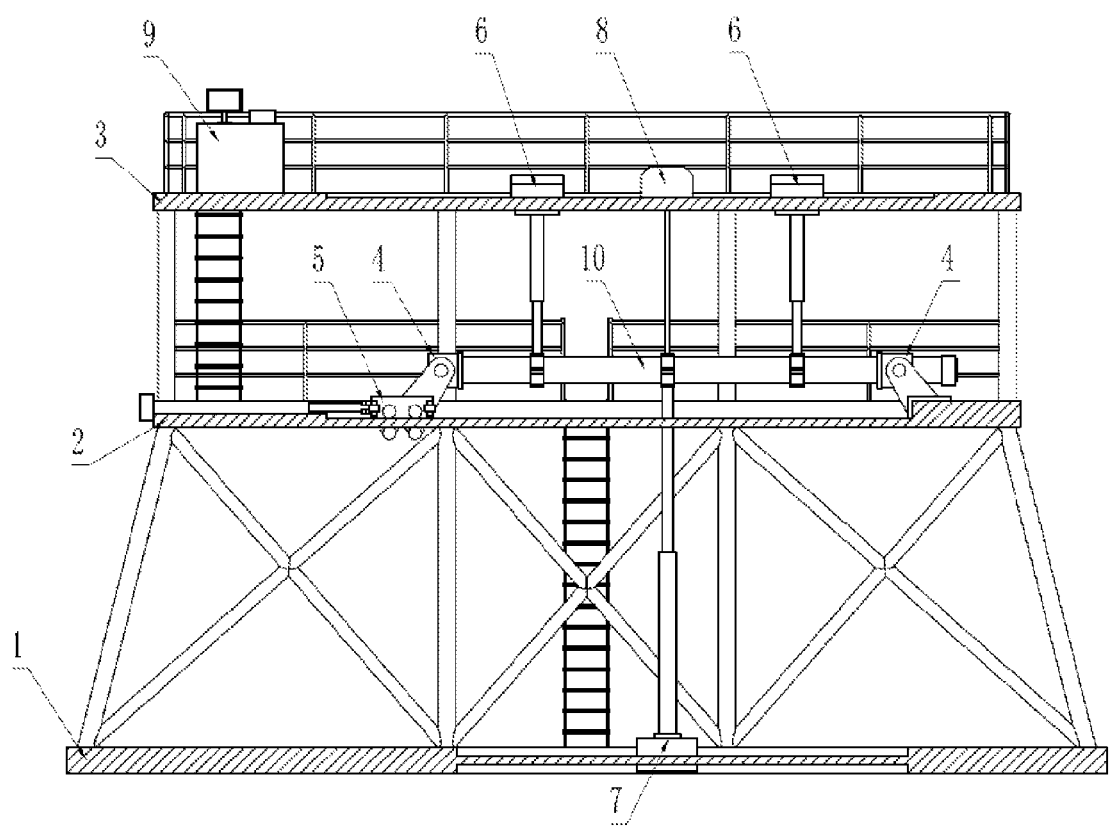
FIG. 2 is a diagram showing the elevation view of an embodiment of the apparatus and methods for umbilical bend-testing.

This document discloses apparatus and methods related to umbilical bend-testing. FIG. 1 and FIG. 2 show the perspective view and elevation view of an implementation of the apparatus and methods for umbilical bend-testing, including a three-level support structure, umbilical terminal locker, bending machine, compression testing device, and stress-strain collecting system. The support structure includes the lower support platform 1, the intermediate support platform 2, the upper support platform 3, and related ladders and handrails. Skidding tracks are arranged on each support platforms for related components. As shown in FIG. 2, the bending machine comprises end-thrust bending device 5 and transverse-tension bending device 7. Two umbilical terminal lockers 4 are equipped on both end, one on the end-thrust bending device and the other on the fixed end of skidding track of the intermediate support platform 2. Two compression testing devices 6 are installed with related V-plates or flat plates and corresponding supports. The compression testing devices 6 also can be used for four-point bending test. Stress-strain collecting system comprises a sensor system 8 and a strain tester system 9 arranged on the upper support platform 3. Umbilical sample 10 is placed on the intermediate support platform 2.

Figure 3:
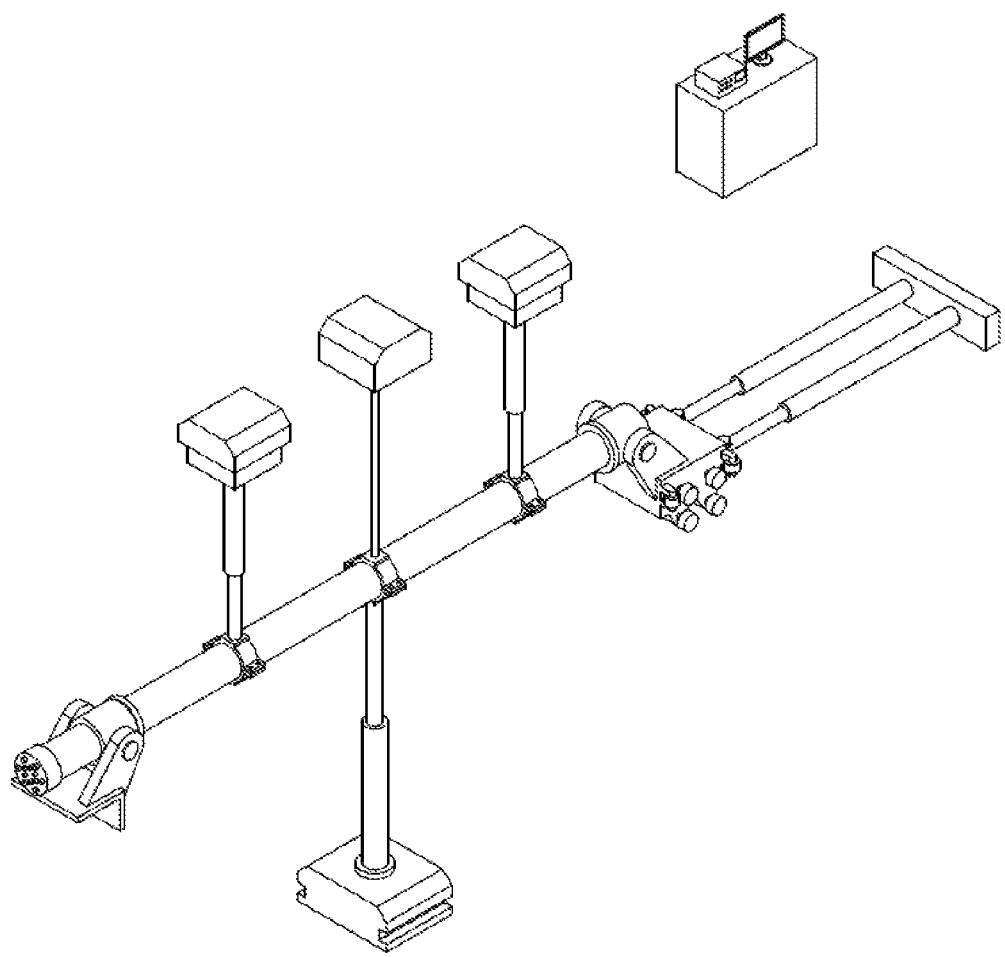
FIG. 3 is a diagram showing an isometric view of an embodiment, without the support structure shown in FIGS. 1 and 2, of the apparatus and methods for umbilical bend-testing.
Figure 4:
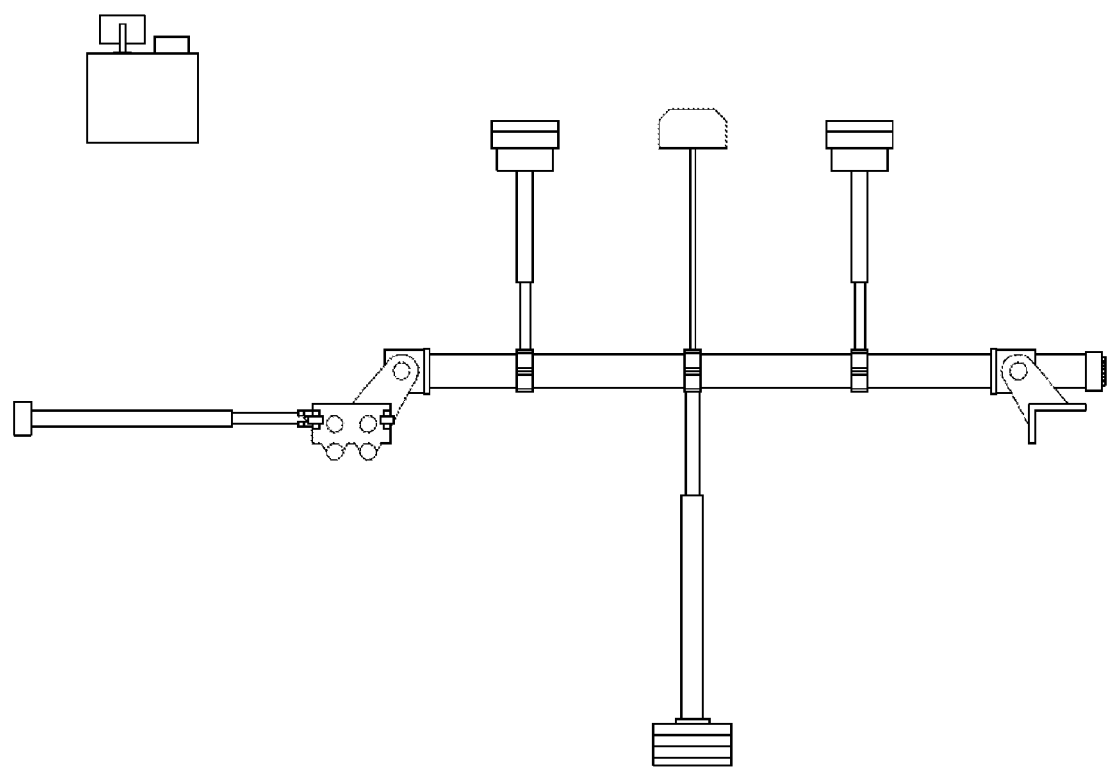
FIG. 4 is a diagram showing an elevation view of an embodiment, without the support structure shown in FIGS. 1 and 2, of the apparatus and methods for umbilical bend-testing.

FIG. 3 and FIG. 4 show the isometric view and elevation view of an implementation of the apparatus and methods for umbilical bend-testing, without the three-level support structure, providing a clear display of the operational components of the implementation.

Figure 5:
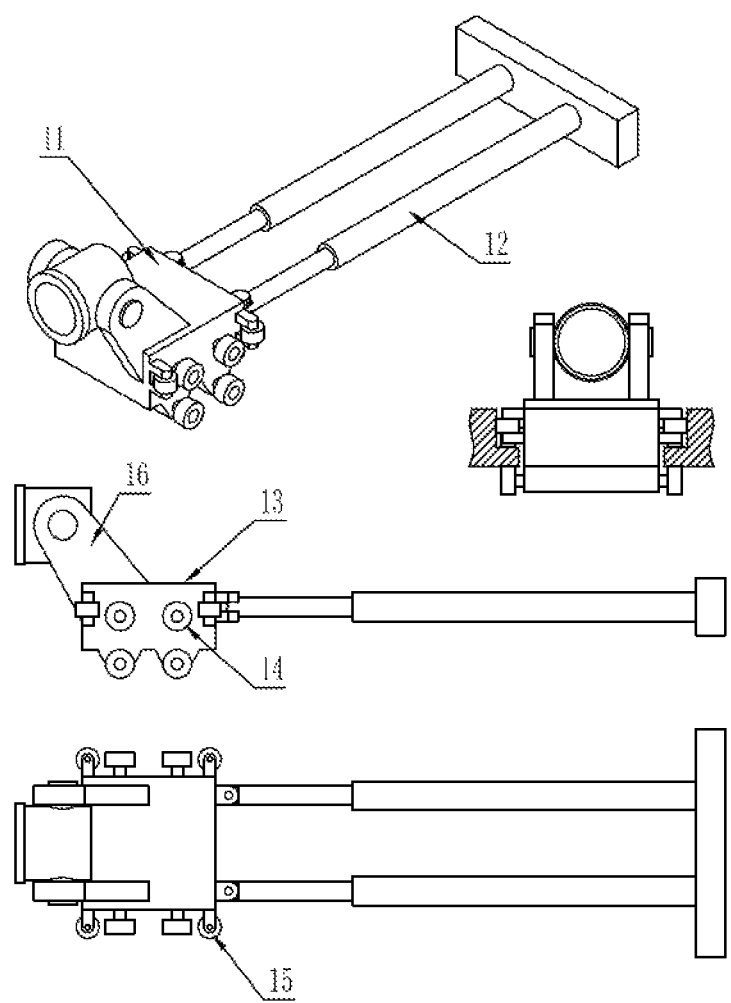
FIG. 5 is a diagram showing various views of an embodiment of the end-thrust bending device of the apparatus and methods for umbilical bend-testing.

As shown in FIG. 5, the end-thrust bending device 5 comprises a travelling trolley 11 and a set of hydraulic arms 12. The guide wheel sets 14 and 15 are installed on the body of the trolley 13, and can grasp the tracks in both horizontal and vertical direction, enabling the trolley 11 to move back and forth under the control of hydraulic arms 12. Rotating support 16 is fixed on one end of the trolley 11, on which an umbilical terminal locker 4 can be installed through the shafts. The umbilical terminal locker 4 can rotate around the shafts for the bending of the umbilical samples.

Figure 6:
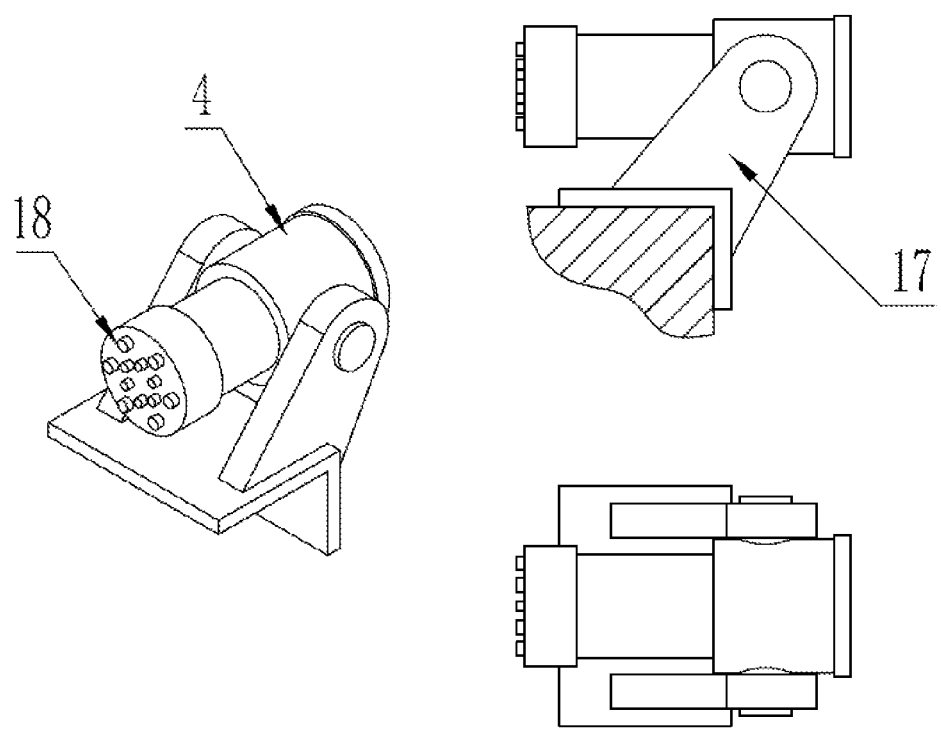
FIG. 6 is a diagram showing various views of an embodiment of the terminal locker of the apparatus and methods for umbilical bend-testing.

FIG. 6 shows the umbilical terminal locker 4 at the fixed end of the umbilical sample 10. The terminal locker 4 can tighten the umbilical, as well as the electric cables, hydraulic pipes and optic fiber connector inside. A fixed rotating support 17 is installed to the end of skidding track on the intermediate support platform 2 by welding or bolts. In addition, customizable quick connectors 18 can be installed to the terminal locker 4 depending on the compositions of the umbilical sample, and can apply internal pressure to the umbilical samples during the test to assist with the analysis of the complex compression performance.

Figure 7:
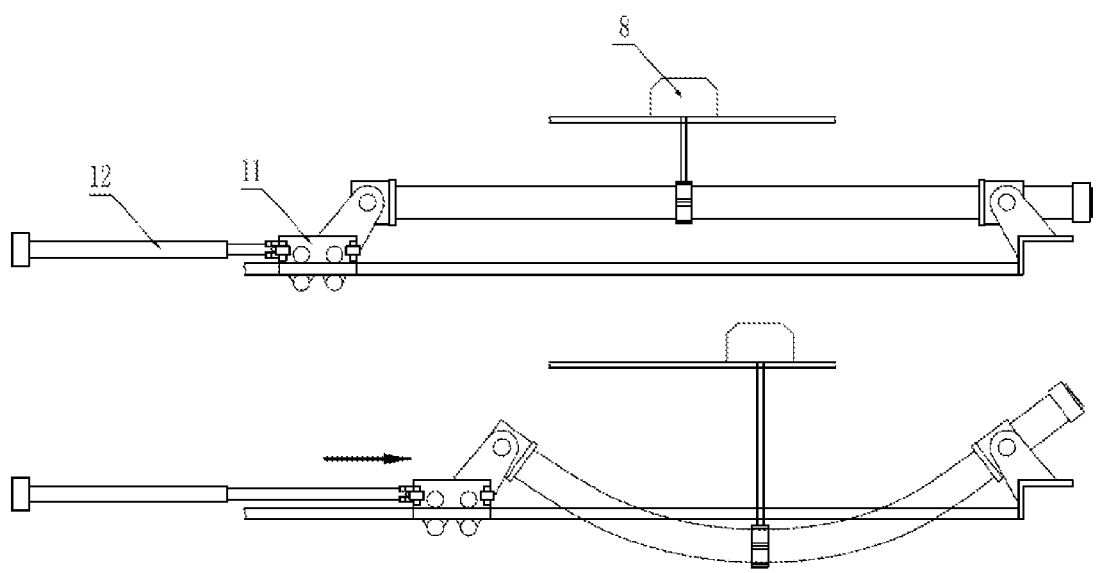
FIG. 7 is a diagram showing the operations of the end-thrust bending device and terminal locker of an embodiment of the apparatus and methods for umbilical bend-testing.

FIG. 7 shows the operations of the end-thrust bending device 5 and terminal locker 4 of an implementation of the apparatus and methods for umbilical bend-testing. The bend-testing can be conducted as follows: connect the travelling trolley 11 and hydraulic arms 12, with the transverse-tension bending device 7 on lower support platform disconnected from the umbilical sample 10; the hydraulic arms 12 can drive the travelling trolley 11 to move back and forth; with the motion of the trolley 11, the umbilical sample 10 is bent with the rotation of the terminal fixer 4 under the effect of gravity; the stress-strain sensor system 8 can be connected to the sample 10 for data collecting, which can then be analyzed by a strain tester system 9; by controlling the frequency and amplitude of the hydraulic arms 12, the end-thrust bending fatigue endurance properties of the umbilical sample 10 can be obtained.

Figure 8:
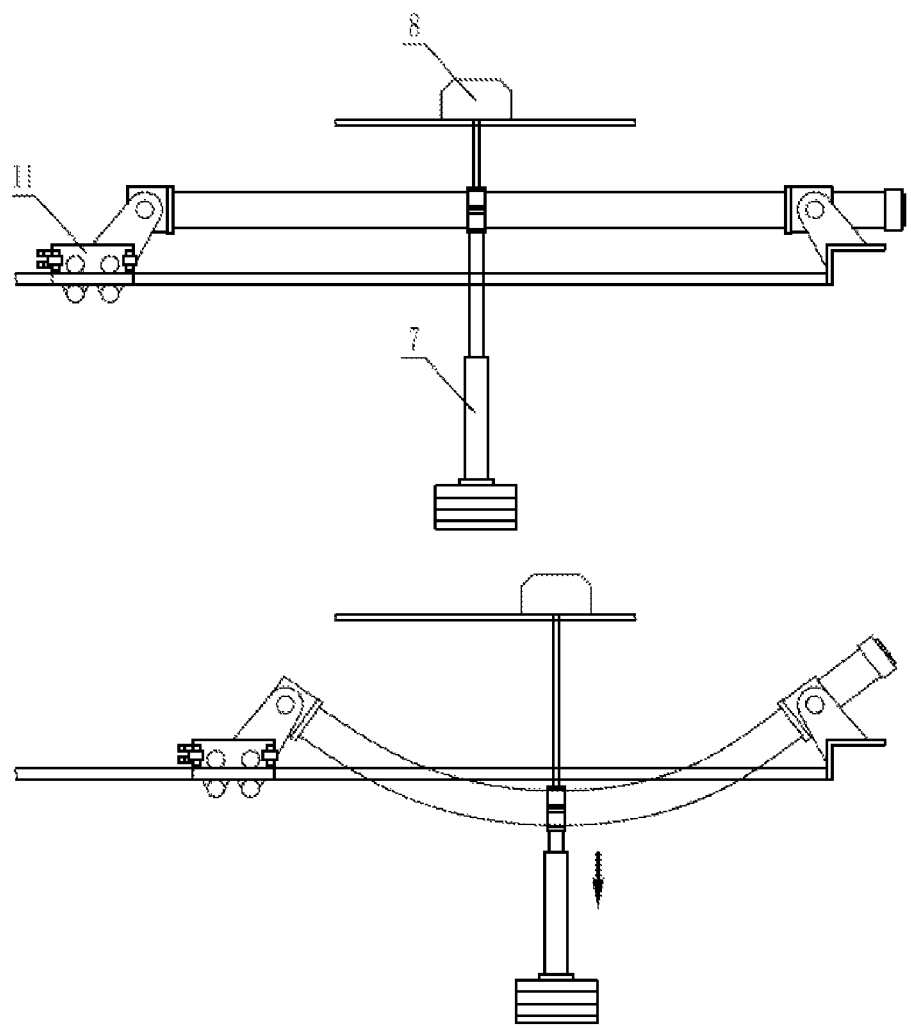
FIG. 8 is a diagram showing the operations of the transverse-tension bending device of an embodiment of the apparatus and methods for umbilical bend-testing.

FIG. 8 shows the operations of the transverse-tension bending device 7 of an implementation of the apparatus and methods for umbilical bend-testing. The bend-testing can be conducted as follows: disconnect the travelling trolley 11 and hydraulic arms 12 and connect the umbilical sample 10 to the hydraulic arm of the transverse-tension bending device 7 using a customized fixture for the umbilical sample 10; the fixture can also connect to the stress-strain collecting system 8 for data collection at the same time, which can then feed the collected data to a strain tester system 9 for analysis; with the motion of the hydraulic arm of the transverse-tension bending device 7, the umbilical sample 10 is pulled to bend; by controlling the frequency and amplitude of the hydraulic arm of the transverse-tension bending device 7, the transverse-tension bending fatigue endurance properties of the umbilical sample 10 can be obtained.

Figure 9:
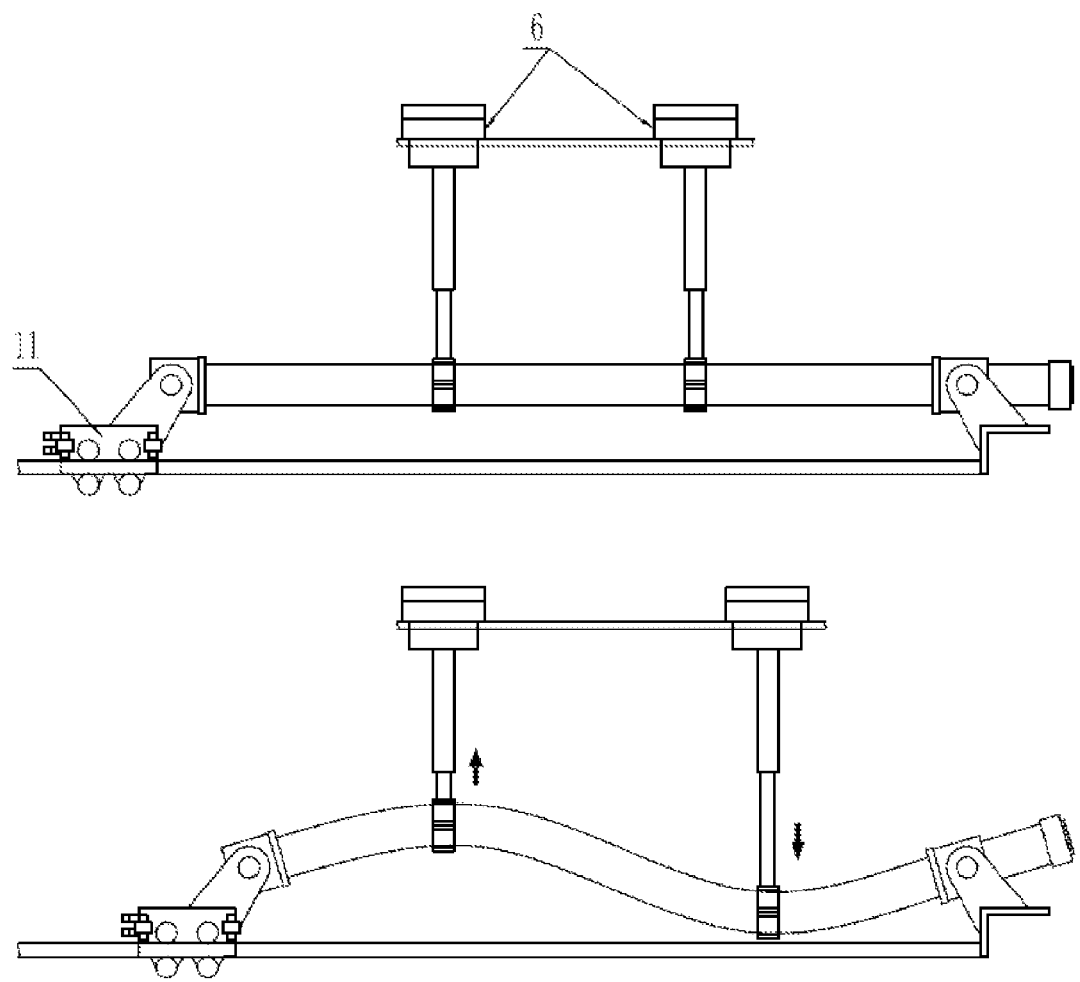
FIG. 9 is a diagram showing the operations of a four-point bending testing of an embodiment of the apparatus and methods for umbilical bend-testing.

FIG. 9 shows the operations of a four-point bending testing of an implementation of the apparatus and methods for umbilical bend-testing. The bend-testing can be conducted as follows: disconnect the travelling trolley 11 from the hydraulic arm 12, disconnect the umbilical sample 10 from the hydraulic arm of the transverse-tension bending device 7, and connect the umbilical sample 10 to the compression testing device 6 using a customized fixture; by controlling the hydraulic arms of the two compression testing devices 6 to extend and shrink asynchronously, four-point bending fatigue endurance test can be conducted on the umbilical sample 10.

Figure 10:
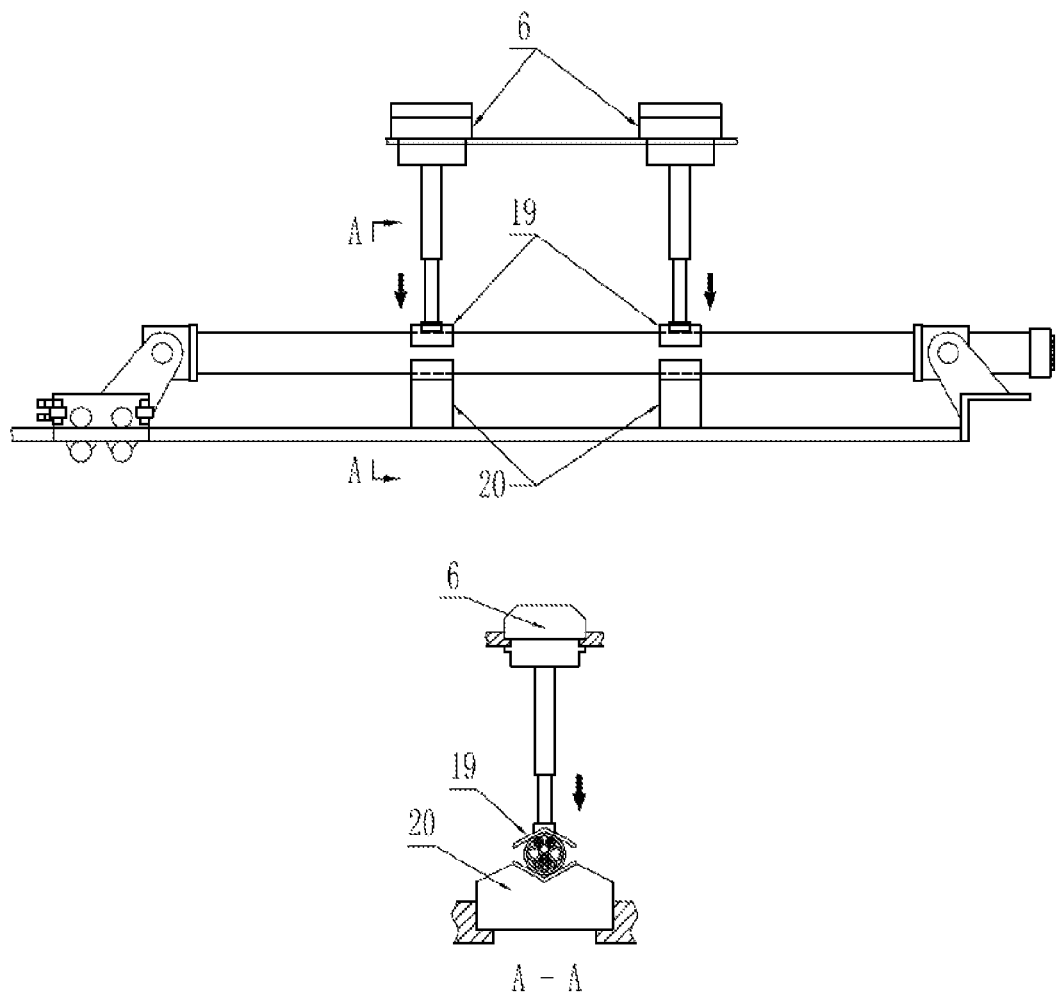
FIG. 10 is a diagram showing the operations of a compression testing of an embodiment of the apparatus and methods for umbilical bend-testing.

FIG. 10 shows the operations of a compression testing of an implementation of the apparatus and methods for umbilical bend-testing. The bend-testing can be conducted as follows: customized V-plate (or flat plate) 19 is installed to the terminal of the hydraulic arm of the compression testing device 6, while a corresponding V-plate (or flat plate) support 20 is arranged on the track on the intermediate platform. The hydraulic arm of the compression testing device 6 extends to apply external pressure to the umbilical sample 10. By controlling the pressure load, the compressive resistance properties of the umbilical sample 10 can be tested. One or two compression testing device 6 can be used as required.

A stress-strain collecting system, including a sensor system 8 and a strain tester system 9, can be arranged on the upper support platform 3. The strain tester system 9 can include a computer with suitable software, which can analyze the stress-strain data collected by the stress-strain sensor system 8 connected to the umbilical sample 10, and obtain the bending fatigue endurance properties of the umbilical sample 10.

In some implementations, the sensor in the sensor system 8 can be a displacement sensor, and can be arranged on the upper support platform 3, and used for testing the minimum bending radius of the umbilical sample 10.

OTHER EMBODIMENTS

Various other adaptations and combinations of features of the embodiments and implementations disclosed are within the scope of the present disclosure. For example, the hydraulic cylinders in the present disclosure can be replaced by any of the tensioning devices that can extend and retract in a controllable way. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for bend-testing a umbilical sample, comprising:
   a support structure;
   a first umbilical terminal locker configured to lock a first end of the umbilical sample, the first umbilical terminal locker being translatable relative to the support structure;
   a second umbilical terminal locker configured to lock a second end of the umbilical sample, the second umbilical terminal locker being non-translatable relative to the support structure;
   a bending machine configured to (1) detachably connect to the first umbilical terminal locker and (2) detachably connect to the umbilical sample between the first and the second ends;
   a compression testing device configured to compress the umbilical sample along a transverse axis of the umbilical sample; and
   a stress-strain data collecting system.

2. An apparatus according to claim 1, wherein the support structure further comprising a lower support platform, an intermediate support platform, an upper support platform, and skidding tracks on said support platforms.

3. An apparatus according to claim 1, further comprising a quick connector installed on the second terminal locker, the quick connector configured to apply an internal pressure to the umbilical sample.

4. An apparatus according to claim 1, wherein the bending machine comprises an end-thrust bending device and a transverse-tension bending device.

5. An apparatus according to claim 4, wherein the end-thrust bending device comprises a connector to connect with the first terminal locker and a trolley moveable by connected hydraulic arms.

6. An apparatus according to claim 1, wherein the compression testing device comprises a fixture that is connected to a hydraulic arm.

7. An apparatus according to claim 6, wherein the fixture is a V-plate or flat plate.

8. An apparatus according to claim 6, wherein a support is provided at the opposite side of the fixture.

9. An apparatus according to claim 1, wherein the stress-strain data collecting system comprises a sensor system and a strain tester system.

10. An apparatus according to claim 9, wherein the sensor system comprises a displacement sensor.

11. An apparatus according to claim 9, wherein the strain tester system further comprises a computer with suitable software for analyzing stress-strain data collected by the sensor system.

12. A method for umbilical bend-testing, comprising:
    connecting two ends of a umbilical sample to two umbilical terminal lockers on a support structure, wherein the umbilical terminal lockers comprise a translatable umbilical terminal locker and a non-translatable umbilical terminal locker;
    connecting a trolley of the end-thrust bending device to the translatable umbilical terminal locker;
    connecting a sensor system to the umbilical sample;
    moving the trolley using one or more hydraulic arms of the end-thrust bending device to push one end of the umbilical sample along a longitudinal axis of the umbilical sample to bend the umbilical sample; and
    analyzing the data obtained from the sensor system using a strain tester system to obtain end-thrust bending fatigue endurance properties of the umbilical sample.

13. A method for umbilical bend-testing, comprising:
    connecting two ends of a umbilical sample to two umbilical terminal lockers on a support structure;

fixing at least one of the two umbilical terminal lockers along a longitudinal axis of the umbilical sample;
connecting a transverse-tension bending device with the umbilical sample using a hydraulic arm with a fixture at its end attaching to the umbilical sample between the two ends;
connecting a sensor system to the umbilical sample;
moving the hydraulic arm to bend the umbilical sample; and
analyzing the data obtained from the sensor system using a strain tester system to obtain transverse-tension bending fatigue endurance properties of the umbilical sample.

14. A method for umbilical bend-testing, comprising:
connecting two ends of a umbilical sample to two umbilical terminal lockers on a support structure;
fixing at least one of the two umbilical terminal lockers along a longitudinal axis of the umbilical sample;
connecting two compression testing devices with the umbilical sample using two hydraulic arms with fixtures at their ends attaching to the umbilical sample between the two ends;
connecting a sensor system to the umbilical sample;
moving the hydraulic arms to bend the umbilical sample; and
analyzing the data obtained from the sensor system using a strain tester system to obtain four-point bending fatigue endurance properties of the umbilical sample.

15. A method for umbilical bend-testing, comprising:
connecting two ends of a umbilical sample to two umbilical terminal lockers on a support structure;
fixing at least one of the two umbilical terminal lockers along a longitudinal axis of the umbilical sample;
connecting a compression testing device with the umbilical sample using a hydraulic arm with a fixture at its end attaching to the umbilical sample between the two ends;
connecting a sensor system to the umbilical sample;
moving the hydraulic arm to apply an external pressure to the umbilical sample; and
analyzing the data obtained from the sensor system using a strain tester system to obtain compressive resistance properties of the umbilical sample.

* * * * *